(12) United States Patent
Sunde et al.

(10) Patent No.: US 11,661,399 B2
(45) Date of Patent: May 30, 2023

(54) METHODS AND COMPOSITIONS FOR PREVENTING DEGRADATION OF DIMETHYL TRISULFIDE

(71) Applicant: Ecolab USA Inc., St. Paul, MN (US)

(72) Inventors: Troy James Sunde, St. Paul, MN (US); Steven James Lange, St. Paul, MN (US); Joelle F. Olson, Shoreview, MN (US)

(73) Assignee: ECOLAB USA INC., St. Paul, MN (US)

( * ) Notice: Subject to any disclaimer, the term of this patent is extended or adjusted under 35 U.S.C. 154(b) by 0 days.

(21) Appl. No.: 16/431,154

(22) Filed: Jun. 4, 2019

(65) Prior Publication Data

US 2019/0367450 A1   Dec. 5, 2019

Related U.S. Application Data

(60) Provisional application No. 62/680,117, filed on Jun. 4, 2018.

(51) Int. Cl.
*C07C 319/26* (2006.01)
*C07C 321/14* (2006.01)

(52) U.S. Cl.
CPC .......... *C07C 319/26* (2013.01); *C07C 321/14* (2013.01)

(58) Field of Classification Search
CPC ........................ C07C 319/26; C07C 321/14
See application file for complete search history.

(56) References Cited

U.S. PATENT DOCUMENTS

| | | |
|---|---|---|
| 1,259,911 A | 3/1918 | Seibert |
| 3,304,646 A | 11/1964 | Staley |
| 3,484,374 A | 12/1969 | Cyba et al. |
| 3,747,260 A | 7/1973 | Lovness |
| 4,217,722 A | 8/1980 | McMullen |
| 4,709,504 A | 12/1987 | Andric |
| 4,800,671 A | 1/1989 | Olson et al. |
| 4,862,638 A | 9/1989 | Stevenson |
| 5,102,662 A | 4/1992 | Gallagher |
| 5,119,586 A | 6/1992 | Townsend |
| 5,438,792 A | 8/1995 | Monett et al. |
| 5,454,186 A | 10/1995 | Gang |
| 5,597,599 A | 1/1997 | Smith et al. |
| 6,063,418 A | 5/2000 | Sugimoto et al. |
| 6,106,821 A | 8/2000 | Baker et al. |
| 6,696,424 B1 | 2/2004 | Wheeler |
| 6,766,612 B1 | 7/2004 | Liu |
| 6,814,956 B2 | 11/2004 | Besser et al. |
| 7,444,711 B2 | 11/2008 | Garcia et al. |
| 7,910,056 B2 | 3/2011 | Ivanine et al. |
| 8,146,290 B1 | 4/2012 | Telly |
| 8,282,952 B2 | 10/2012 | Smit |
| 8,413,370 B2 | 4/2013 | Messian |
| 8,661,728 B2 | 3/2014 | Borth et al. |
| 8,789,309 B2 | 7/2014 | Fabry |
| 8,808,721 B2 | 8/2014 | Banfield et al. |
| 8,931,206 B2 | 1/2015 | Olson et al. |
| 8,966,812 B2 | 3/2015 | McKnight |
| 9,125,392 B2 | 9/2015 | Olson et al. |
| 9,901,088 B2 | 2/2018 | Backmark et al. |
| 10,123,534 B2 | 11/2018 | Olson et al. |
| 10,136,631 B2 | 11/2018 | Thuis et al. |
| 2003/0033965 A1 | 2/2003 | Van Lint |
| 2004/0216367 A1 | 11/2004 | Klein |
| 2005/0138858 A1 | 6/2005 | Lyng |
| 2006/0086038 A1 | 4/2006 | Mosher |
| 2006/0283076 A1 | 12/2006 | Chambers et al. |
| 2007/0044372 A1 | 3/2007 | Lang et al. |
| 2007/0254907 A1 | 11/2007 | Bowles |
| 2008/0052982 A1 | 3/2008 | Windsor |
| 2008/0115406 A1 | 5/2008 | Duston et al. |
| 2008/0269177 A1 | 10/2008 | Bessette |
| 2008/0319029 A1 | 12/2008 | Richman et al. |
| 2009/0145019 A1 | 6/2009 | Nolen et al. |
| 2009/0145020 A1 | 6/2009 | McKnight |
| 2009/0223115 A1 | 9/2009 | Lang et al. |
| 2009/0313883 A1 | 12/2009 | Olson et al. |
| 2010/0011655 A1 | 1/2010 | Frisch |
| 2010/0212213 A1 | 8/2010 | Hope, III et al. |

(Continued)

FOREIGN PATENT DOCUMENTS

| | | |
|---|---|---|
| CA | 2130375 A1 | 4/1995 |
| CN | 202026723 U | 11/2011 |

(Continued)

OTHER PUBLICATIONS

Adler et al., Modified Atmospheres. In: Alternatives to pesticides in stored-product IPM, (edited by Subramanyam and Hagstrum), Kluwer Academic Publishers, Boston, pp. 105-146 (2000).
Anderson, J.F. et al., A carbon dioxide, heat and chemical lure trap for the bedbug, Cimex lectularius, Medical and Veterinary Entomology, vol. 23, pp. 99-105 (2009).
Barcay, S.J. and Olson, J.F., From Detection through Protection: Solutions for Fighting Bed Bug Infestations, 13 pgs. (2010).
Bayer Environmental Science, Need to Know, Temprid® SC now labeled for Bed Bugs, vol. 7, No. 1, 2 pages (Feb. 18, 2010).
Cardinal Professional Products, ECO2FUME®, http://www.cardinalproproducts.com/eco2fume.htm, 2 pages, printed Mar. 30, 2011.

(Continued)

*Primary Examiner* — Ana Z Muresan
(74) *Attorney, Agent, or Firm* — Merchant & Gould P.C.

(57) ABSTRACT

The present disclosure provides methods and compositions for inhibiting degradation of dimethyl trisulfide (DMTS) in solution. Concentrate compositions include DMTS and polar inorganic or organic solvent. The compositions can be stored in containers for at least 2 weeks at 54° C. or at least one year at room temperature and less than 50% of the DMTS degrades. The concentrate compositions can be diluted for use and combined with other components to form various solutions.

6 Claims, 12 Drawing Sheets

(56) References Cited

U.S. PATENT DOCUMENTS

| | | |
|---|---|---|
| 2011/0072712 A1 | 3/2011 | Black et al. |
| 2011/0105333 A1 | 5/2011 | Israels et al. |
| 2011/0113674 A1 | 5/2011 | Levy |
| 2011/0203159 A1 | 8/2011 | McKnight |
| 2011/0289822 A1 | 12/2011 | Duehl et al. |
| 2012/0012046 A1 | 1/2012 | Cain |
| 2012/0110894 A1 | 5/2012 | Black et al. |
| 2012/0186137 A1 | 7/2012 | Schneidmiller et al. |
| 2012/0192479 A1 | 8/2012 | Schmitz |
| 2012/0210628 A1 | 8/2012 | Park et al. |
| 2012/0233907 A1 | 9/2012 | Pattison et al. |
| 2012/0240451 A1 | 9/2012 | Ricks |
| 2012/0285076 A1 | 11/2012 | Banfield |
| 2012/0301532 A1 | 11/2012 | Carey et al. |
| 2013/0031825 A1 | 2/2013 | Dass |
| 2013/0067796 A1 | 3/2013 | Dong et al. |
| 2013/0180161 A1 | 7/2013 | Vasudeva et al. |
| 2013/0184153 A1 | 7/2013 | Dieleman et al. |
| 2013/0232849 A1 | 9/2013 | Schmacher |
| 2013/0291427 A1 | 11/2013 | Prohaska |
| 2013/0312313 A1 | 11/2013 | Lefkowitz et al. |
| 2014/0020278 A1 | 1/2014 | Smith |
| 2014/0020280 A1 | 1/2014 | Cullen |
| 2014/0033597 A1 | 2/2014 | Vasudeva et al. |
| 2014/0041284 A1 | 2/2014 | Nugent |
| 2014/0187425 A1 | 7/2014 | Allen et al. |
| 2014/0216367 A1 | 8/2014 | Norman et al. |
| 2014/0290123 A1 | 10/2014 | Duff |
| 2014/0311016 A1 | 10/2014 | Wang et al. |
| 2015/0007485 A1 | 1/2015 | Hortel et al. |
| 2015/0290143 A1 | 10/2015 | Petrikovics et al. |
| 2015/0297535 A1 | 10/2015 | Petrikovics et al. |
| 2015/0366210 A1* | 12/2015 | Olson ............... A01M 1/02 43/132.1 |
| 2016/0316750 A1 | 11/2016 | Gries et al. |
| 2017/0251655 A2 | 9/2017 | Frutos et al. |
| 2017/0253744 A1 | 9/2017 | Ishida et al. |

FOREIGN PATENT DOCUMENTS

| | | |
|---|---|---|
| EP | 0 416 255 A1 | 3/1991 |
| KR | 10-2008-0036963 | 4/2008 |
| KR | 10-2010-0092641 | 8/2010 |
| KR | 10-2013-0122739 | 11/2013 |
| WO | 97/24034 A2 | 7/1997 |
| WO | 2005/070209 A1 | 8/2005 |
| WO | 2008/030385 A2 | 3/2008 |
| WO | 2009/047584 A1 | 4/2009 |
| WO | 2009/075839 A1 | 6/2009 |
| WO | 2012/162703 A1 | 11/2012 |
| WO | 2013/115719 A1 | 8/2013 |
| WO | 2014/028835 A2 | 2/2014 |
| WO | 2015/089661 A1 | 6/2015 |
| WO | 2015/195395 | 12/2015 |

OTHER PUBLICATIONS

Continental Carbonic, Use Dry Ice to Remove Bed Bugs, http://www.continentalcarbonic.com/dryice/remove-bed-bugs-dry-ice.php, 1 page, printed Sep. 20, 2010.

D.C. Robacker, "Attraction of both sexes of Mexican fruit fly, *Anastrepha ludens*, to a mixture of ammonia, methylamine, and putrescine," Journal of Chemical Ecology, vol. 19, No. 12, (1993).
Extended European Search Report for Application No. 12796003.7 dated Feb. 13, 2015.
Extended European Search Report for Application No. 17158799.1 dated Sep. 7, 2017.
Extended European Search Report for Application No. 15809461.5 dated Oct. 19, 2017.
Extended European Search Report for Aplication No. 15751451.4 dated Dec. 4, 2017.
FMC Corporation, Best Management Practices, Bed Bugs, 2009 (3 pages).
Gangloff-Kaufmann et al. Bed Bugs in America: A Pest Management Industry Survey. American Entomologist, vol. 52, No. 2, pp. 105-106 (Summer 2006).
Gries et al., "Bed Bug Aggregation Pheromone Finaly Identified," Angewandte Chemie International Edition, pp. 1-5 (Dec. 21, 2014).
Gries et al., Supporting Information Bed Bug Aggregation Pheromone Finaly Identified, Angewandte Chemie International Edition, 24 pages (Dec. 21, 2014).
International Search Report and Written Opinion for PCT/IB2012/052756 dated Jan. 29, 2013.
International Search Report and Written Opinion for PCT/US2015/017115 dated Jun. 1, 2015.
International Search Report and Written Opinion for International Application No. PCT/US2015/034715 dated Sep. 1, 2015.
Luckow, "Scientists Developing Pheromone-Laced Bed Bug Trap," Pest Control Technology, 2 pages (Jun. 2015).
MGK® Product Code 027911, Material Safety Data Sheet, Bedlam™ Insecticide, Feb. 28, 2006 (2 pages).
National Center for Healthy Housing, What's Working for Bed Bug Control in Multifamily Housing: Reconciling best practices with research and the realities of implementation, (3 pages: cover page, table of contents, and p. 22) (before Oct. 20, 2011).
Penn State University, Dept of Entomology, Entomological Notes, Bed Bugs, http://ento.psu.edu/extension/factsheets/bedbugs, printed Apr. 13, 2010 (4 pages).
Pest Management Professional, The Business of Bed Bugs, Michael F. Potter, Jan. 1, 2008 (8 pages).
Snell, Eric J., Smith, Todd, Sexton, Wally, Eclosion of Bed Bug (*Cimex lectularius*) Eggs after Exposure to Various Compounds, Snell Scientifics LLC, Meansville, GA, submitted paper at the National Conference on Urban Entomology in Tulsa, OK, May 18-21, 2008 (1 page).
Stern Environmental Group, Bed Bug Control Services for Hotels, Motels, and Apartment Buildings; http://www.stemenvironmental.com/bedbugs/commercial.php, 3 pages, printed Sep. 20, 2010.
TARR Status Report, U.S. Appl. No. 77/771,410, Registration No. 3751703, mark:Bedlam Insecticide, printed Apr. 12, 2010 (2 pages).
Tvedten, Steve, The Bug Stops Here, http://www.getipm.com/thebestcontrol/bugstop/control_bed_bugs.htm, 2 pages, printed Sep. 20, 2010.
www.bed-bug.net, Bed Bug Killer/How to Kill Bed Bugs/Bed Bug Information, printed Apr. 13, 2010 (1 page).
International Search Report and the Written Opinion of the International Searching Authority, PCT/US2019/035394, dated Aug. 13, 2019.
Database WPI, Week 201062, Thomson Scientific, London, (2010).
Database WPI, Week 201665 Thomson Scientific, London, 2016.

* cited by examiner

METHODS AND COMPOSITIONS FOR PREVENTING DEGRADATION OF DIMETHYL TRISULFIDE

CROSS-REFERENCE TO RELATED APPLICATION

This application claims the benefit of U.S. Provisional Application No. 62/680,117, filed Jun. 4, 2018, which is hereby incorporated by reference in its entirety.

TECHNICAL FIELD

The present disclosure relates generally to methods and compositions for preventing degradation of dimethyl trisulfide (DMTS) in solution.

BACKGROUND

Dimethyl trisulfide (DMTS) is a volatile sulfur compound. DMTS has a foul odor that is associated with cooked onion, Limburger cheese, and aged beer. DMTS is produced by decomposing bacteria and decomposing mammals. Insects and flies of various species are attracted to the scent of DMTS.

DMTS has been discovered to be a component of insect pheromones. In particular, DMTS attracts insects that feed on blood, such as bed bugs. DMTS can be combined with other chemical compounds to enhance the attractive properties of DMTS. In some cases, DMTS is combined with MDEA (methyl diethanolamine) or other amines to more effectively attract insects such as bed bugs. Once the insects have been attracted, they can be trapped or exterminated.

There are difficulties in storing DMTS in solution. Existing solutions of DMTS alone or combined with MDEA are not stable when dissolved in water. Over time, DMTS decomposes and disappears from the solution. There is a need for improved methods of storing DMTS in a solution.

It is against this background that the present disclosure is made. Techniques and improvements are provided herein.

SUMMARY

In summary, the present disclosure relates to methods and compositions for decreasing degradation of dimethyl trisulfide (DMTS) in solution. Various aspects are described in this disclosure, which include, but are not limited to, the following aspects.

In one aspect, a single-phase concentrate composition includes at least 10 ppm DMTS and at least 10 wt-% polar organic solvent. The DMTS does not degrade more than 40% within one year of storage and the concentrate composition is phase-stable in containers.

In another aspect, a single-phase concentrate composition includes at least 10 ppm DMTS and an amine and at least 80 wt-% polar organic solvent. The DMTS and amine do not degrade more than 40% within one year of storage and the concentrate composition is phase-stable in containers.

In another aspect, a single-phase composition includes DMTS and a pH of 9 or less. When the pH is 9 or less, the composition does not degrade more than 40% within one year of storage and is phase-stable in containers when the carrier is water, a polar organic solvent, or both.

In another aspect, a single-phase composition includes DMTS and an amine, and a pH of 4 or less. When the pH is 4 or less, the composition does not degrade more than 40% within one year of storage and is phase-stable in containers when the carrier is water, a polar organic solvent, or both.

In another aspect, a container for housing the compositions is substantially free of materials that cause degradation of DMTS.

In another aspect, a method of making an insect pheromone solution includes diluting a concentrate composition with water, polar organic solvent, or both.

This summary is provided to introduce a selection of concepts in a simplified form that are further described below in the Detailed Description. This summary is not intended to identify key features or essential features of the claimed subject matter, nor is it intended to be used to limit the scope of the claimed subject matter.

DETAILED DESCRIPTION

Figure 1:
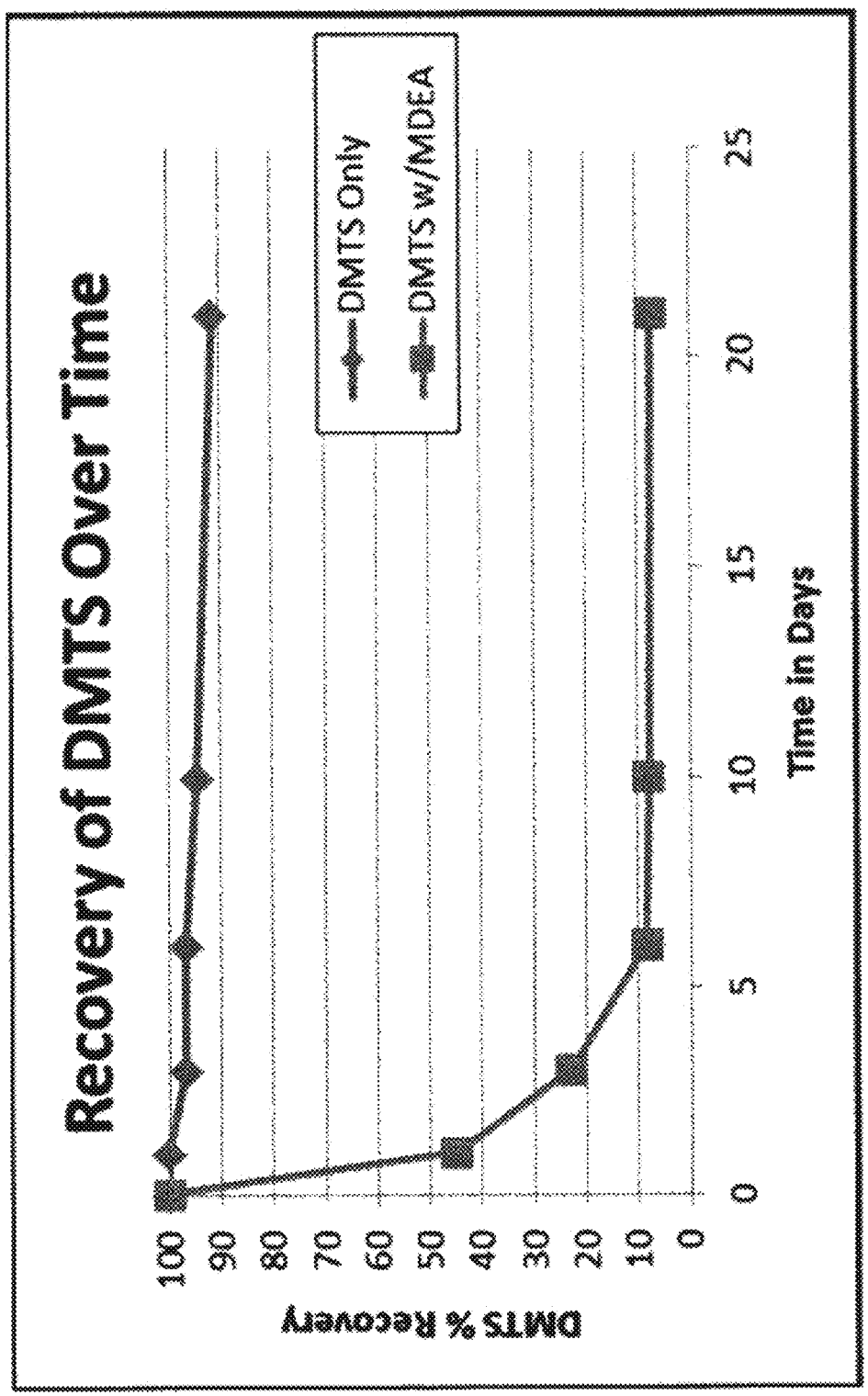
FIG. 1 is a line graph showing DMTS recovery over time with or without MDEA.

Various embodiments will be described in detail. Reference to various embodiments does not limit the scope of the claims attached hereto. Additionally, any examples set forth in this specification are not intended to be limiting and merely set forth some of the many possible embodiments for the appended claims.

The present disclosure relates to compositions including dimethyl trisulfide (DMTS). The compositions and containers provided herein create stable storage conditions for solutions including DMTS. DMTS is stored in a solution with polar inorganic and/or organic solvent, optionally in containers that do not promote degradation of DMTS.

EPA accelerated stability guidelines provide that two weeks of storage at 54° C. is equivalent to one year of storage at room temperature. The compositions and methods provided herein provide solutions including DMTS that are shelf stable for at least one year.

In some aspects, the DMTS in the solutions does not degrade more than 60% over the course of one year. In some embodiments, the DMTS degrades less than 50%, less than 40%, or less than 30% during one year of storage. In some formulations, a DMTS solution is provided where less than 20% of the DMTS degrades over the course of a year. In some instances, less than 10% or less than 5% of the DMTS in the composition is degraded.

It was found previously that DMTS degrades more rapidly under certain conditions. For instance, DMTS degrades more rapidly when stored in non-fluorinated HDPE (plastic) containers as compared to glass containers. DMTS also degrades more rapidly when it is combined with MDEA than when it is in a separate solution. Various solvents and pH levels of the solution including DMTS were investigated. The variables of solvent, pH, and container material were further examined, as described in the Examples below, to determine improved compositions and methods of storage for DMTS solutions that prevent DMTS degradation.

Compositions

Compositions utilized in the present disclosure provide for stable storage of DMTS. When packaged in proper containers, the compositions show reduced degradation after 2 weeks of storage at 54° C. as compared to existing solutions. These storage conditions mimic storage at room temperature for one year, according to EPA guidelines. Compositions according to the present disclosure are stored either as concentrates which are later diluted for use, or a ready-to-use solutions that do not require further dilution before use. The concentrate compositions can be diluted with any appropriate solvent. In some embodiments, the concentrate compositions are diluted with water to produce use solutions. In some instances, use solutions including DMTS can be combined with one or more additional components to produce insect pheromone solutions and insecticide solutions.

Compositions according to the present disclosure include at least DMTS and a diluent that can be a polar inorganic solvent (e.g., water) or a polar organic solvent. Additional ingredients can include amines and other functional ingredients. In some embodiments, water is limited or excluded from the concentrate compositions.

Dimethyl Trisulfide

Dimethyl trisulfide (DMTS) can be used as an insect attractant or pesticide. DMTS is hydrophobic and does not dissolve readily into water.

Concentrate compositions of the present disclosure include at least 10 ppm DMTS. In some aspects, concentrate compositions can include at least 20 ppm or at least 30 ppm DMTS. The concentrate compositions can include at least 50 ppm, at least 100 ppm, or at least 300 ppm DMTS. In some embodiments, concentrate compositions according to the present disclosure include no more than 30,000 ppm DMTS. The concentrate compositions, in some aspects, include no more than 10,000 ppm DMTS, no more than 6,000 DMTS, or no more than 3,000 ppm DMTS. In some aspects, the concentrate compositions include from 30 ppm to 10,000 ppm DMTS. Some concentrate compositions include from 100 ppm to 3,000 ppm or from 300 ppm to 1,000 ppm DMTS.

The concentrate compositions can be diluted to form use compositions or solutions. The diluted use compositions can include at least 0.3 ppm DMTS or at least 0.5 ppm DMTS. In some aspects, the use compositions include at least 0.7 ppm, at least 0.9 ppm, or at least 1.5 ppm DMTS. Use compositions can include at least 3 ppm, at least 5 ppm, or at least 7 ppm DMTS. The diluted use compositions include no more than 3,000 ppm DMTS. In some aspects, the use compositions include no more than 1,000 ppm, no more than 500 ppm, or no more than 300 ppm DMTS. Use compositions may include no more than 200 ppm, no more than 100 ppm, or no more than 50 ppm DMTS in some aspects. Single-phase use compositions can include from 1 ppm to 1000 ppm DMTS. In some aspects, the use compositions include from 3 ppm to 500 ppm DMTS, or from 5 ppm to 100 ppm DMTS. In some aspects, the use compositions include from 10 ppm to 50 ppm DMTS.

Polar Organic Solvent

Compositions of the present disclosure optionally include organic solvents. In some embodiments, the organic solvents are polar organic solvents. Polar organic solvents suitable for use in the present concentrate compositions include ethanol, propanol, isopropanol, propylene glycol, ethylene glycol, glycerin, butyl cellosolve, butyl carbitol, diethylene glycol monoethyl ether, ethylene glycol monoethyl ether, and n-butanol. Other polar organic solvents can be used in the concentrate compositions. In some aspects, the polar organic solvent is an alcohol. In some aspects, the polar organic solvent is selected from ethanol, propylene glycol, and mixtures thereof. The polar organic solvents can provide stability to the DMTS.

Concentrate compositions according to the present disclosure may include at least 50 wt-% polar organic solvent. In some aspects, the compositions include at least 60 wt-% or at least 75 wt-% polar organic solvent. The concentrate compositions can include at least 90 wt-% polar organic solvent. In some embodiments, the concentrate compositions include at least 95 wt-% or at least 98 wt-% polar organic solvent. In some aspects, the concentrate compositions include from 95 wt-% to 99 wt-% polar organic solvent. In some aspects, the concentration compositions are free of polar organic solvent.

Single-phase use compositions may include at least 1 wt-% polar organic solvent. In some embodiments, at least 5 wt-% or at least 10 wt-% polar organic solvent is included in use compositions. Use compositions may include no more than 50 wt-%, no more than 40 wt-%, or no more than 30 wt-% polar organic solvent. In some aspects, no more than 20 wt-% or no more than 10 wt-% of the use composition is polar organic solvent.

Polar Inorganic Solvent

In some embodiments, the concentrate compositions include 50 wt-% or less polar inorganic solvent. Generally, the polar inorganic solvent is water. In some embodiments, the concentrate compositions include 50 wt-% or less, less than 30 wt-%, less than 25 wt-%, or less than 10 wt-% water. Improved stability of DMTS is achieved when the concentrate compositions include less than 5 wt-% or less than 1 wt-% water. Some concentrate compositions can be free of water. In other embodiments, the concentrate compositions may include 50 wt-% to 99 wt-% water. The concentrate composition may only include water as the diluent.

The compositions can be formulated as use compositions. Alternatively, concentrate compositions can be diluted with polar inorganic solvent to form use compositions. The polar inorganic solvent is generally water, but could include other suitable solvents. Use compositions include at least 50 wt-%, at least 60 wt-%, or at least 70 wt-% polar inorganic solvent. In some embodiments, the use compositions include less than 90 wt-% water.

Amine

In some embodiments, the concentrate compositions can include amine. Amines can be selected from the group consisting of include trimethylamine (TMA), isopropylamine, trimethanolamine, monoethanolamine (MEA), diethanolamine (DEA), triethanolamine (TEA), methyl diethanolamine (MDEA), bicine (2-(bis(2-hydroxyethyl)amino) acetic acid), and histamine. Some amines can function as insect pheromones.

In some aspects, the amine is an alkanolamine. Suitable alkanolamines include methyl diethanolamine (MDEA), monoethanolamine (MEA), diethanolamine (DEA), triethanolamine (TEA) and mixtures thereof. In some aspects, the amine is MDEA.

In some embodiments, concentrate compositions of the present disclosure optionally include at least 120 ppm amine. In some aspects, concentrate compositions include at least 240 ppm amine or at least 480 ppm amine. The concentrate compositions include no more than 120,000 ppm amine. In some aspects, the concentrate compositions include no more than 60,000 ppm or no more than 30,000 ppm amine. The concentrate compositions include from 120 ppm to 1,200 ppm amine.

Use compositions can optionally include at least 1.2 ppm amine. In some aspects, the use compositions include at least 2.4 ppm, at least 3.6 ppm, at least 4.8 ppm, or at least 6 ppm amine. Use compositions according to the present disclosure include no more than 1,200 ppm amine. In some aspects, use compositions include no more than 900 ppm, no more than 600, or no more than 300 ppm amine. In some aspects, use compositions include from 2 ppm to 200 ppm amine. Use compositions can include from 3 ppm to 100 ppm amine.

pH Adjusting Agents

The compositions may optionally include a pH adjusting agent, which is typically an acid. Neutral to acidic pH values have been found to reduce the DMTS degradation, even in the presence of water without polar organic solvent. The acid may be an organic acid such as acetic, malic, citric, lactic, formic, or hydroxyacetic acid, or inorganic acid such as phosphoric, sulfuric, nitric, or hydrochloric acid. In some embodiments, it may be desirable to buffer the composition using phosphate, citrate, acetate, malate, lactate, or formate buffers. If a source of alkalinity is needed to adjust the pH to a neutral pH, sodium or potassium hydroxide or a carbonate such as sodium or potassium carbonate or bicarbonate could be used provided that the pH is not increased too much. A pH above 9 has been found to increase the degradation of DMTS. Concentrate compositions according to the present disclosure have a pH of at least 1. The concentrate compositions have a pH of no more than 9. In some embodiments, the concentrate compositions have a pH in the range of 1 to 9, 2 to 8, 2 to 7, 1 to 4, or 6 to 9.

Other Ingredients

Additional ingredients can be included in the concentrate compositions. For example, additional ingredients can include carriers, surfactants, emulsifiers, drying agents, film forming agents, and combinations thereof. In some embodiments, the concentrate compositions include a pesticide or insecticide.

Exemplary Compositions

TABLE 1

Concentrate Compositions

| | Formula A (wt-%) | Formula B (wt-%) | Formula C (wt-%) | Formula D (wt-%) |
| --- | --- | --- | --- | --- |
| DMTS | 0.001-3 | 0.003-0.6 | 0.01-0.1 | 0.001-3 |
| Polar Organic Solvent | 50-99.999 | 75-99.997 | 90-99.989 | 0 |
| Amine | 0-12 | 0-2.4 | 0.001-0.4 | 0-12 |
| Acid | 0-10 | 0-2.4 | 0.001-0.4 | 0-10 |
| Water | 0-30 | 0-20 | 0.1-10 | Balance |

TABLE 2

Use Compositions

| | Formula A (ppm) | Formula B (ppm) | Formula C (ppm) | Formula D (ppm) |
| --- | --- | --- | --- | --- |
| DMTS | 0.3-3,000 | 3-500 | 10-50 | 0.3-3,000 |
| Polar Organic Solvent | 10,000-500,000 | 50,000-300,000 | 100,000-200,000 | 0 |
| Amine | 0-12,000 | 0-600 | 1.2-200 | 0-12,000 |
| Acid | 0-10,000 | 0-600 | 1.2-200 | 0-10,000 |
| Water | Balance | Balance | Balance | Balance |

Storage

Storage conditions can also affect the stability of DMTS in solution. DMTS solutions are stored in containers. Some container materials cause degradation of DMTS. Some container materials accelerate DMTS degradation faster than others. Packaged concentrate compositions including DMTS preferably utilize containers for housing the concentrate composition that are substantially free of materials that cause degradation of DMTS. In some embodiments, the container is a dispenser. The container can be a metal container or a glass container. Preferably, the container is not a plastic container.

In some embodiments, the container is a fluorinated HDPE container. The container can be fluorinated at level 3. The container can be fluorinated at level 5. Preferably, the container is not a non-fluorinated HDPE container.

Packaged concentrate compositions are phase stable. In some embodiments, single-phase concentrate compositions according to the present disclosure are phase-stable in containers.

DMTS does not degrade more than 40% within one year of normal storage conditions at ambient temperature in concentrate compositions. When stored at 54° C., DMTS in concentrates does not degrade more than 30% within two weeks. In some embodiments, DMTS in concentrate compositions does not degrade more than 20% within one year of storage at room temperature.

DMTS in use compositions does not degrade more than 60% in one year at ambient temperature. In some aspects, DMTS in use compositions does not degrade more than 50%.

Methods

Methods of inhibiting degradation of dimethyl trisulfide (DMTS) involve preparation of a concentrate composition. The DMTS is combined with a polar inorganic or organic solvent to form a concentrate, as described above. The DMTS in solution is stable in storage in containers for one year at ambient temperature (about 15°-25° C.). The containers are preferably made of the materials described above, which do not cause degradation of DMTS.

Methods of making insect pheromone solutions are also described. Any of the concentrate compositions described above are diluted with polar inorganic solvent, such as water. In some embodiments, at least 120 ppm amine is added to the use solution. In some aspects, the amine is MDEA. Insecticide can be added to the concentrate or use solution to exterminate insects that are attracted to the pheromone.

Concentrate compositions according to the present disclosure are stable in storage for up to 2 weeks when stored at a temperature of 54° C. This simulates storing the composition at room temperature for up to one year. In some embodiments, the concentrate compositions are stable for greater than a year when stored at room temperature or ambient temperature (about 20°-25° C.). For best results, concentrate compositions are diluted with water immediately before use.

EXAMPLES

Accelerated Stability Storage Condition Setup

EPA accelerated stability guidelines call for storage of compositions at 54° C. for two weeks. This is considered to be the equivalent to storing compositions for one year at room temperature. These conditions were applied to the following studies to ensure that DMTS can be formulated in compliance with EPA guidelines.

Example 1

It was previously observed that DMTS breaks down when stored in solution with water, regardless of the type of container in which it is stored. In particular, DMTS combined with MDEA showed accelerated breakdown of DMTS in water. It was hypothesized that the presence of MDEA accelerated the breakdown of DMTS. A comparison was performed between DMTS alone and DMTS with MDEA.

FIG. 1 shows a comparison of recovery of DMTS over time. 120 ppm DMTS only is compared to 120 ppm DMTS with 420 ppm MDEA. Using the accelerated conditions described above, DMTS in water was still observed to be degrading over time. However, the degradation was slowed significantly compared to the formula mixed with MDEA. It was determined that separating DMTS into its own solution helped significantly with stability.

Example 2

Various conditions were modified to improve the overall stability of DMTS in solution. First, the pH was lowered by buffering the solution. It was predicted that a lower pH might prevent the catalyzation of DMTS breakdown. The solution was buffered to a pH of 6 and compared to a control. 32 ppm DMTS was stored in glass at 40° C. for 7 days, then stored at 54° C. for an additional 15 days.

Figure 2:
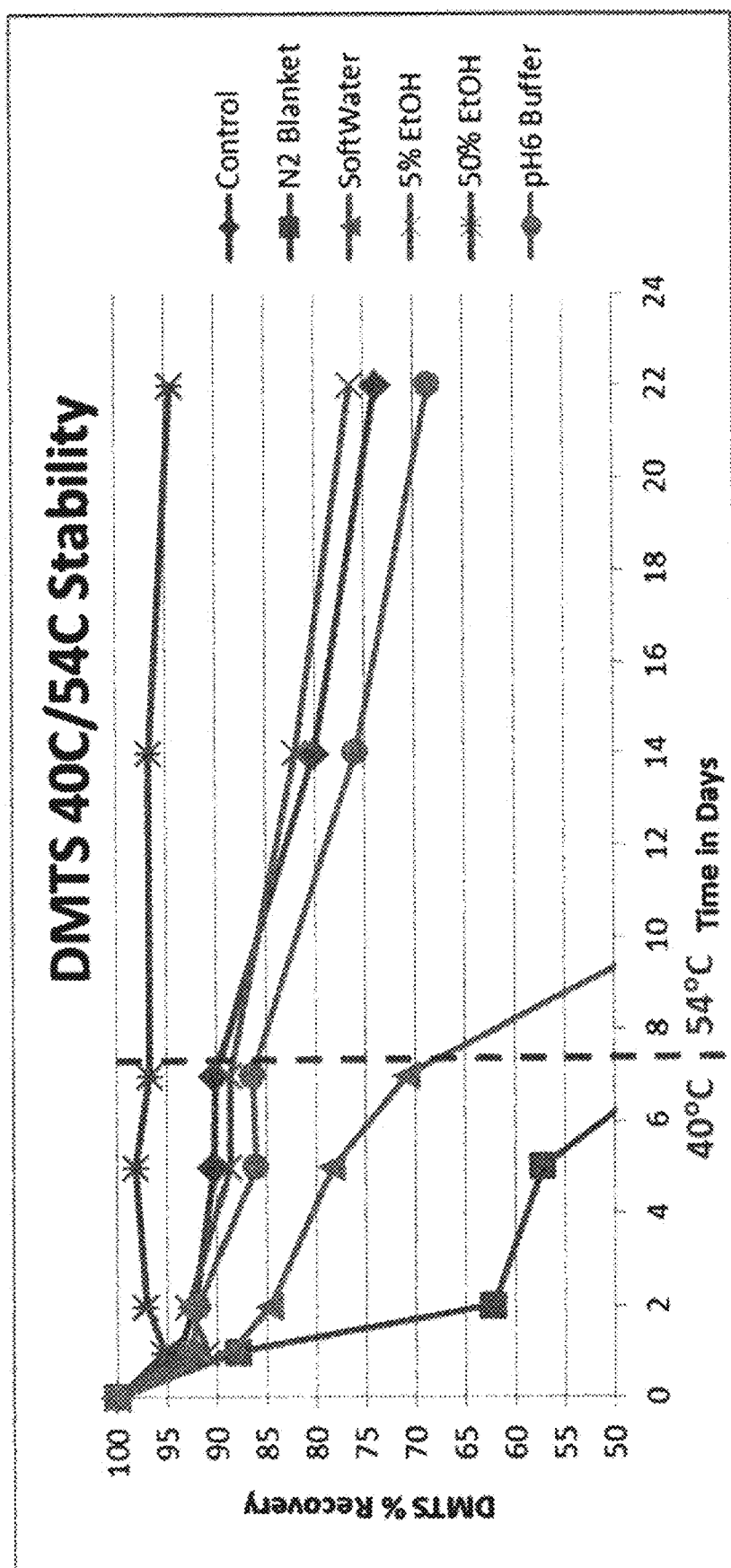
FIG. 2 is a line graph showing DMTS recovery over time in various solvent conditions.

The results are shown in FIG. 2. The samples using N2 blanket and soft water provided the least stable conditions for DMTS. The samples in which DMTS was in solution with ethanol showed the least degradation. The sample with the pH 6 buffer had faster breakdown than the control. Rather than improving stability, the buffer ions may have contributed to greater breakdown of DMTS.

Example 3

DMDS was added to the DMTS in this example. It was hypothesized that if the breakdown pathway of DMTS to DMDS exists in equilibrium, additional DMDS would stabilize the breakdown pathway. DMDS was added to formulas containing DMTS only and DMTS with MDEA.

Figure 3:
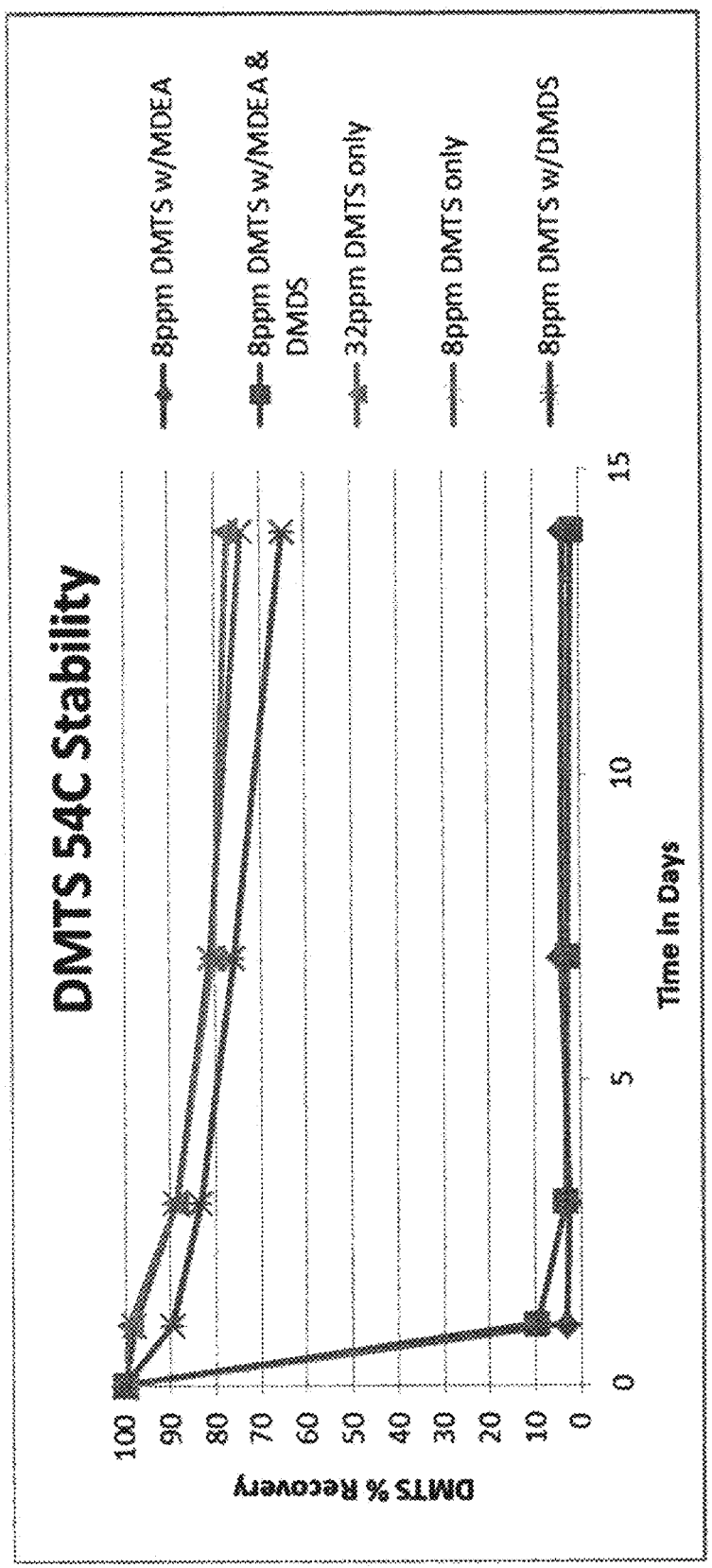
FIG. 3 is a line graph showing DMTS recovery over time comparing concentrations of DMTS and MDEA.

The results are shown in FIG. 3. The addition of DMDS did not slow down the breakdown of DMTS. This suggests that the breakdown pathway of DMTS is irreversible.

Example 4

The results in Example 2 suggested that ethanol could slow degradation of DMTS. It was hypothesized that propylene glycol (PG) could have a similar effect. Samples were prepared with 8 ppm and 4 ppm DMTS in water as controls. Experimental samples included 8 ppm DMTS with 1% PG or 10% PG. A sample was also prepared in an HDPE container that was not fluorinated.

Figure 4:
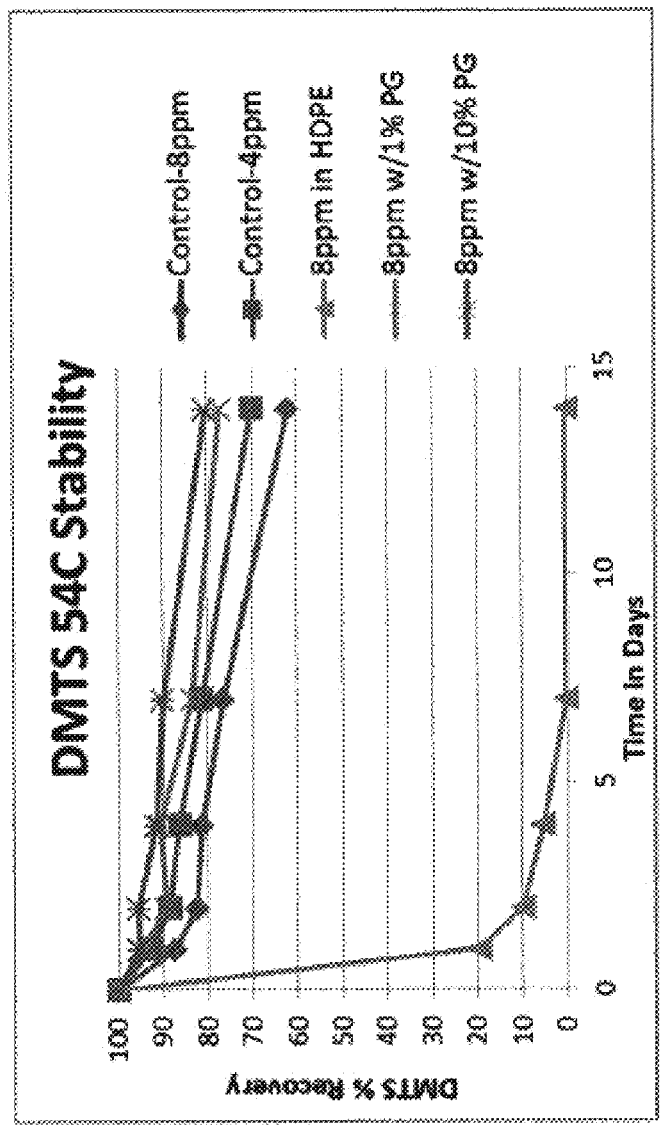
FIG. 4 is a line graph showing DMTS recovery over time comparing concentrations of DMTS and propylene glycol.

The results are shown in FIG. 4. Some improvement was seen with the use of PG, with greater benefit being seen with the higher concentration of PG. The sample in the HDPE container showed significantly faster degradation of DMTS at 54° C. This suggested that non-fluorinated HDPE containers are not helpful in slowing degradation of DMTS in solution.

Example 5

This example examined the effects of fluorination of HDPE containers on the stability of DMTS. Stability of DMTS was recorded for storage at 54° C. over the course of 14 days. Glass containers were used as a control. HDPE containers were tested having no fluorination (F0), Level 3 fluorination (F3), and Level 5 fluorination (F5). Samples of DMTS were prepared to a dilution of 8 ppm DMTS in water with 10% PG.

Figure 5:
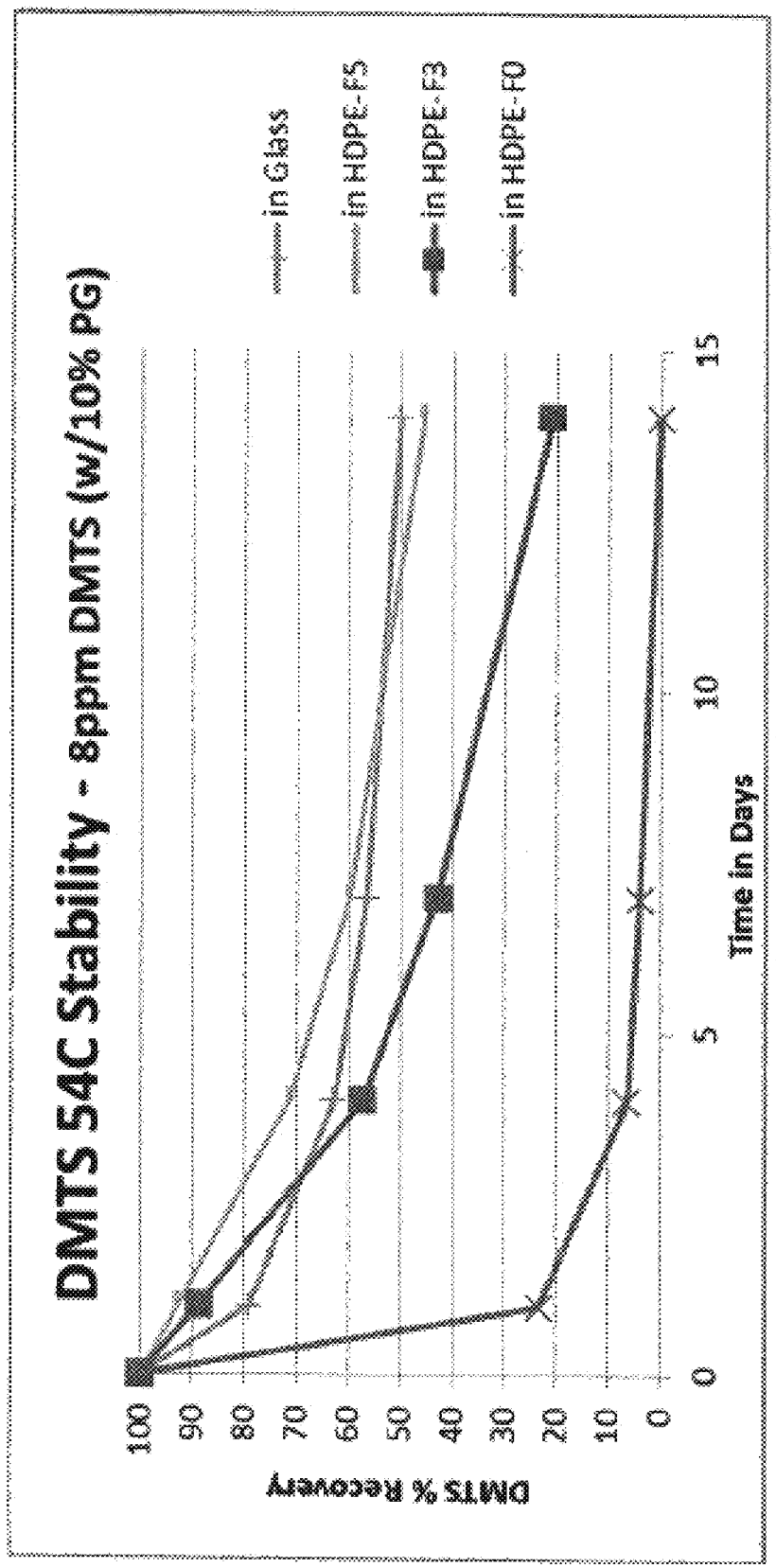
FIG. 5 is a line graph showing DMTS recovery over time comparing fluorination levels of HDPE containers.

The results are shown in FIG. 5. The non-fluorinated HDPE containers showed the fastest rates of DMTS degradation. The samples stored in HDPE with Level 5 fluorination showed the best results which were similar to the glass containers.

Example 6

Given the improvements seen with 10% PG used as solvent, higher concentrations of PG were tested. 0.28% DMTS in 100% PG was tested for stability over two weeks at 54° C. Storage in glass containers was compared to HDPE containers with Level 3 fluorination.

Figure 6:
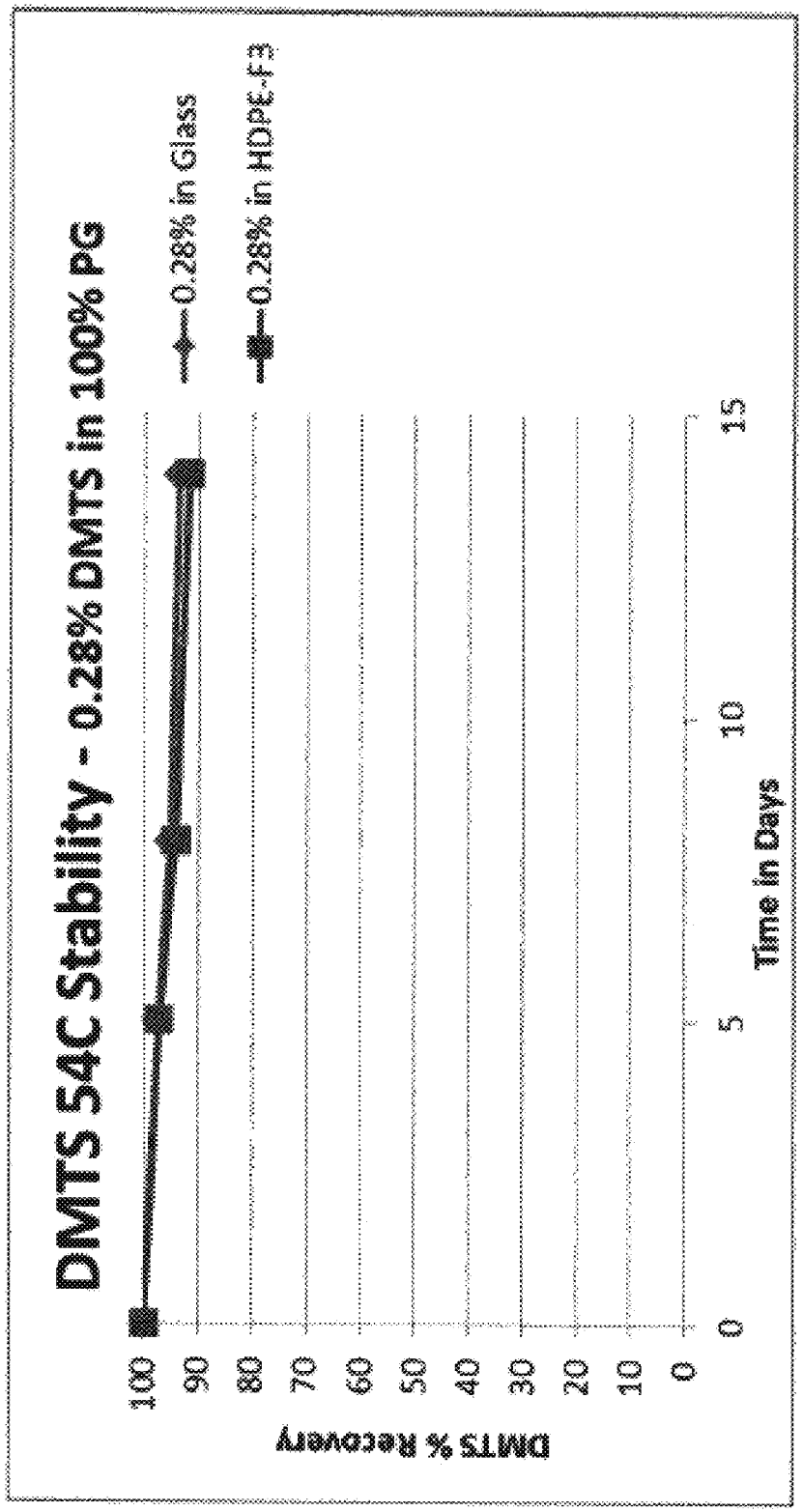
FIG. 6 is a line graph showing DMTS recovery over time comparing glass with fluorinated HDPE containers.

The results are shown in FIG. 6. Similar stability results were observed for each type of container. The percent recovery remained above 90% over 14 days, showing a marked improvement over the previous experiments using 10% PG.

Example 7

Other solvents were tested without dilution with water. Samples of 0.03% DMTS were prepared in 100% solvent. The solvents tested were ethanol in a glass container, PG in a glass container, PG in a non-fluorinated HDPE container, and glycerol in a glass container.

Figure 7:
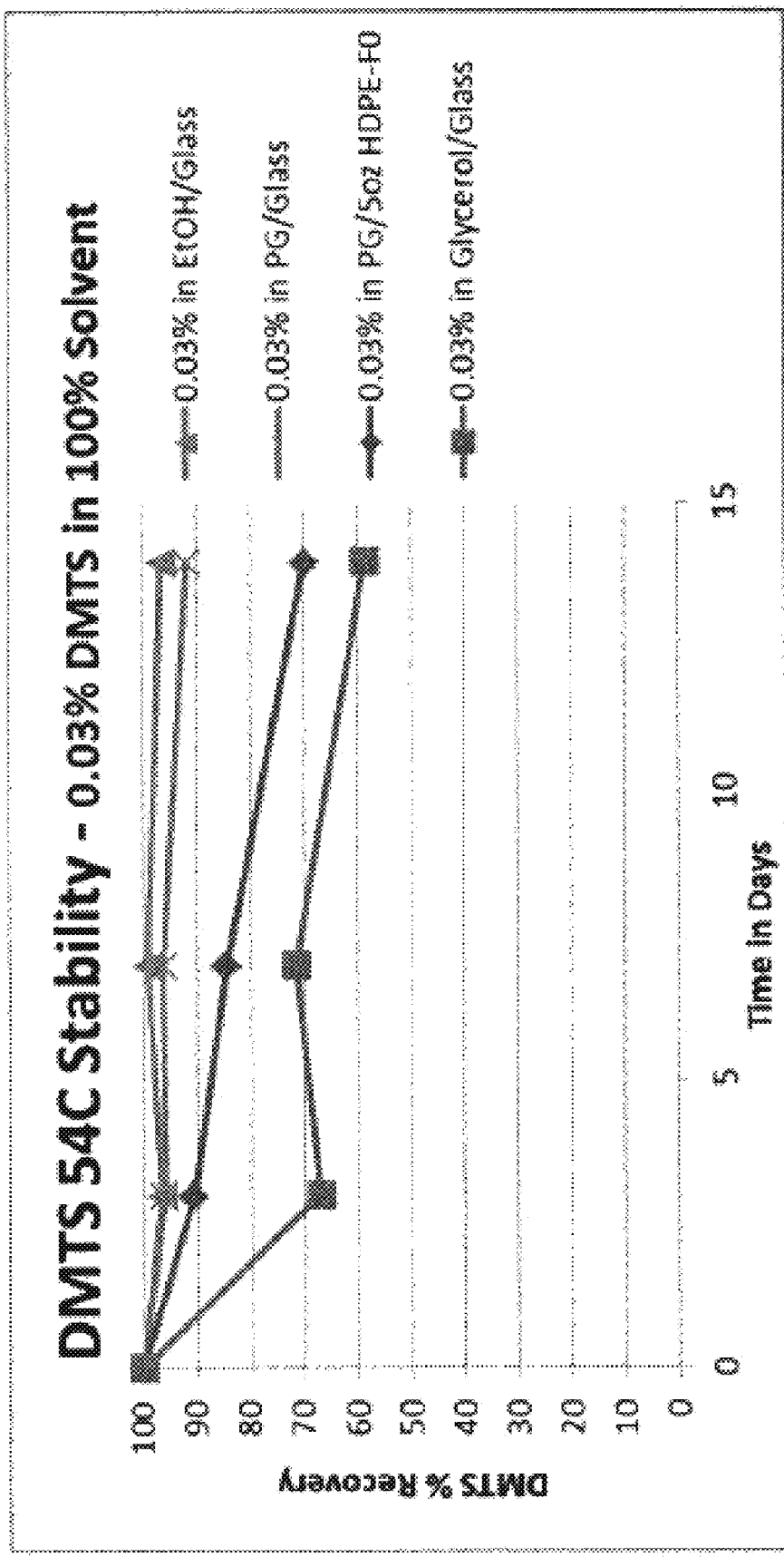
FIG. 7 is a line graph showing DMTS recovery over time comparing storage containers and solvents.

The results are shown in FIG. 7. Greater than 90% recovery of DMTS was observed with 100% ethanol or propylene glycol in glass containers. The least 50% DMTS recovery was achieved with glycerol in glass containers.

Overall, increased concentrations of solvents other than water greatly improved the stability of DMTS in solution. Studies indicate that higher solvent content allows for higher concentrations of DMTS to be used in formulas without concerns for stability. Additionally, the studies of container materials indicate that HDPE bottles fluorinated at levels 3 or 5 perform similarly to glass containers for maintaining stability of DMTS.

Example 8

Figure 8:
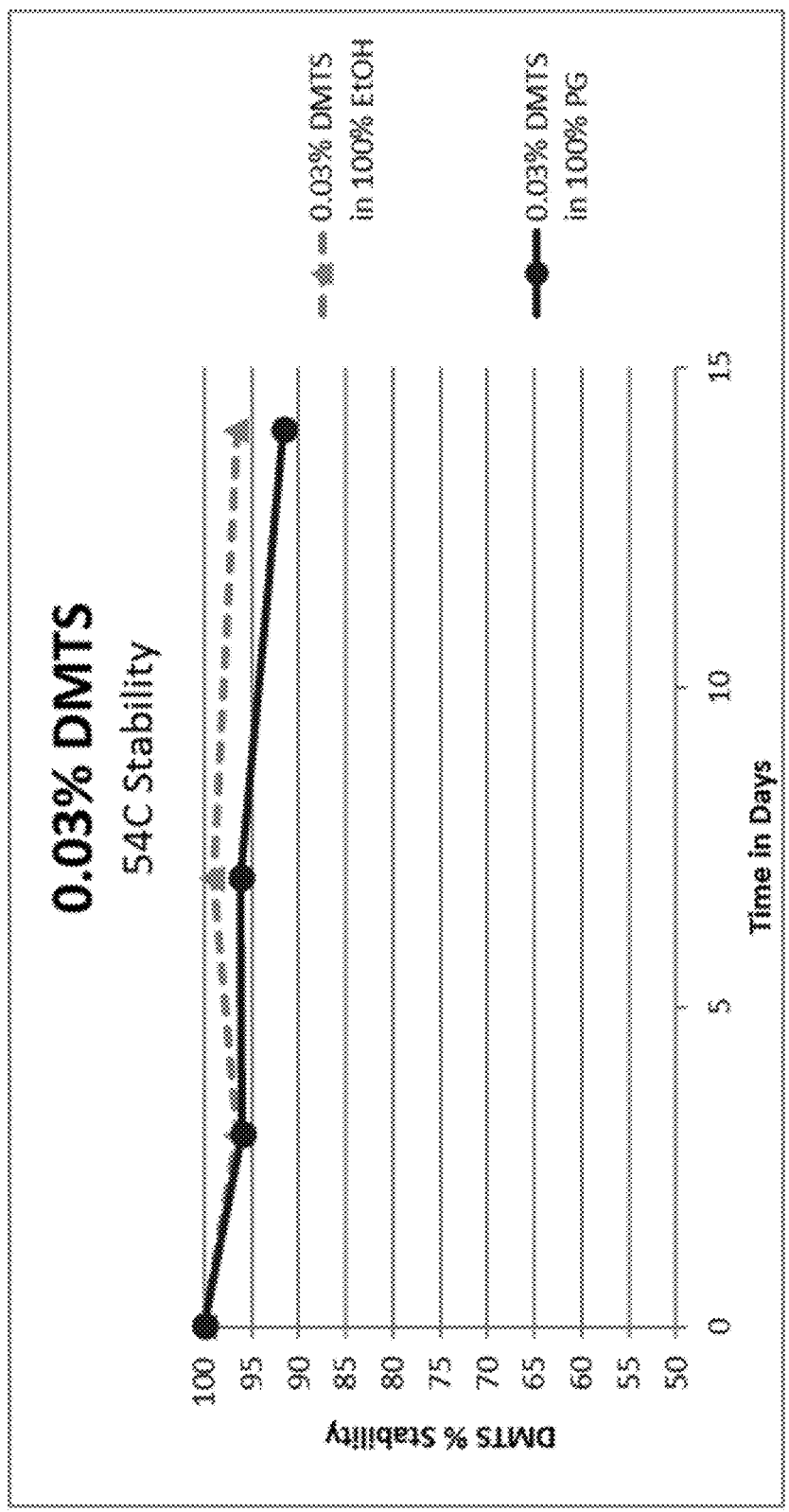
FIG. 8 is a line graph showing DMTS recovery over time comparing 100% polar organic solvents.

In this example, 0.03 wt-% (300 ppm) DMTS was dissolved into solvent consisting of 100% ethanol (EtOH) or 100% propylene glycol (PG). This study is very similar to Example 7. Recovery of DMTS was recorded over the course of 14 days. The DMTS solutions were stored in the accelerated conditions of 54° C. The results are shown in FIG. 8. Less than 10% DMTS was degraded over the course of 14 days for both EtOH and PG. The DMTS dissolved in EtOH showed slightly better stability.

Example 9

Figure 9:
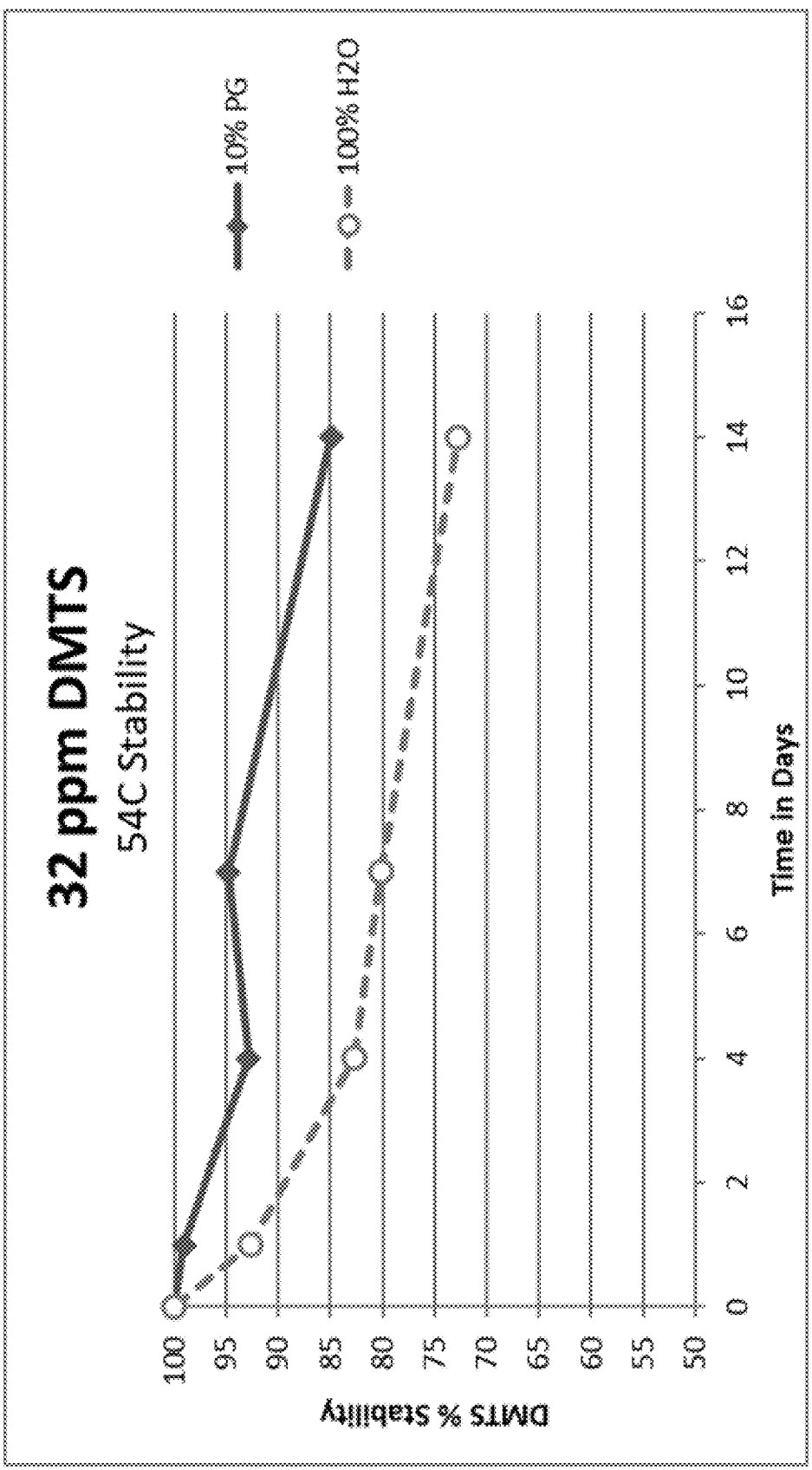
FIG. 9 is a line graph showing DMTS recovery over time comparing solvents having different concentrations of propylene glycol in water.
Figure 10:
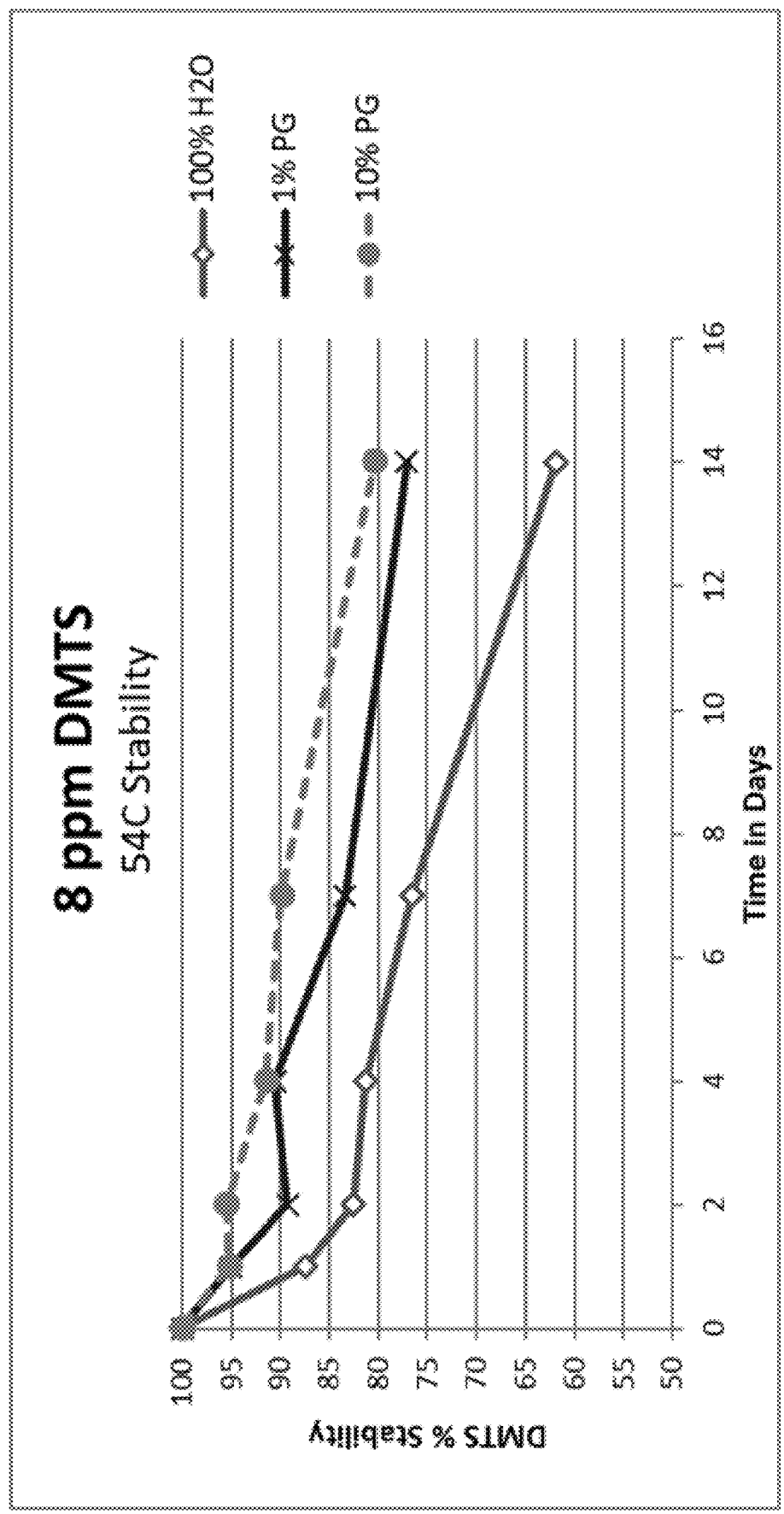
FIG. 10 is a line graph showing DMTS recovery over time comparing solvents having different concentrations of propylene glycol in water.

In this example, a lower concentration of DMTS was used to produce a use composition. 32 ppm DMTS was dissolved in either a 100% water solution or a combination of 10% PG and 90% water. The same accelerated conditions were used for 14 days. The results are shown in FIG. 9. Over 70% of DMTS was recovered with water as the only solvent. However, using a 10% PG solution in water improved DMTS stability, providing greater than 80% recovery. This study indicates that dilution of the concentrate composition does have a negative effect on DMTS stability, but that use compositions still maintain relatively high stability.

Example 10

Even lower concentrations of DMTS were examined to determine if further dilution of the concentrate affects stability of DMTS. Solutions including 8 ppm DMTS were prepared. DMTS was dissolved in water, a solution of 1 wt-% PG in water, and a solution 10 wt-% PG in water. Greater than 60% recovery of DMTS was achieved with all samples. Solutions including PG showed higher levels of stability, with the 10% PG solution providing greater than 80 wt-% recovery. The reduced quantity of DMTS did have a slight negative effect on stability.

Figure 11:
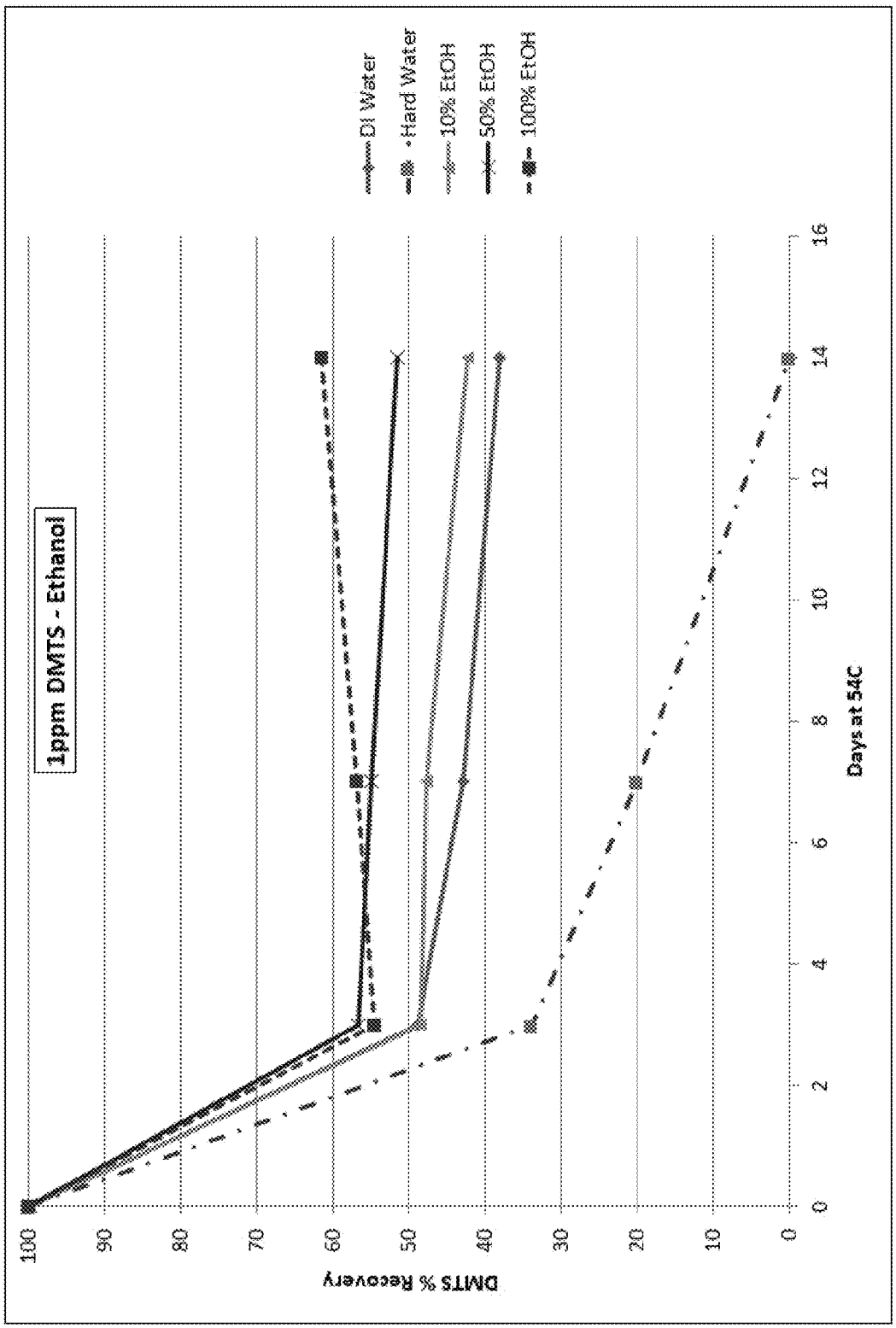
FIG. 11 is a line graph showing DMTS recovery over time comparing solvents having different concentrations of polar organic solvents in water.

Finally, solutions including 1 ppm DMTS were examined to determine if use compositions including small amounts of DMTS can remain stable over the course of the two week testing period at 54° C. FIG. 11 shows the results for diluting the 1 ppm DMTS in water, ethanol, or both. Hard water had the greatest negative effect on DMTS stability. By day 14, no DMTS remained in the solution. Deionized (DI) water resulted in less than 40% recovery of DMTS. Addition of ethanol to the water produced more stable solutions of DMTS, but even at 100% EtOH, the DMTS solutions could only achieve 60% recovery after 14 days. This indicates that DMTS is less stable when in more dilute solutions.

Figure 12:
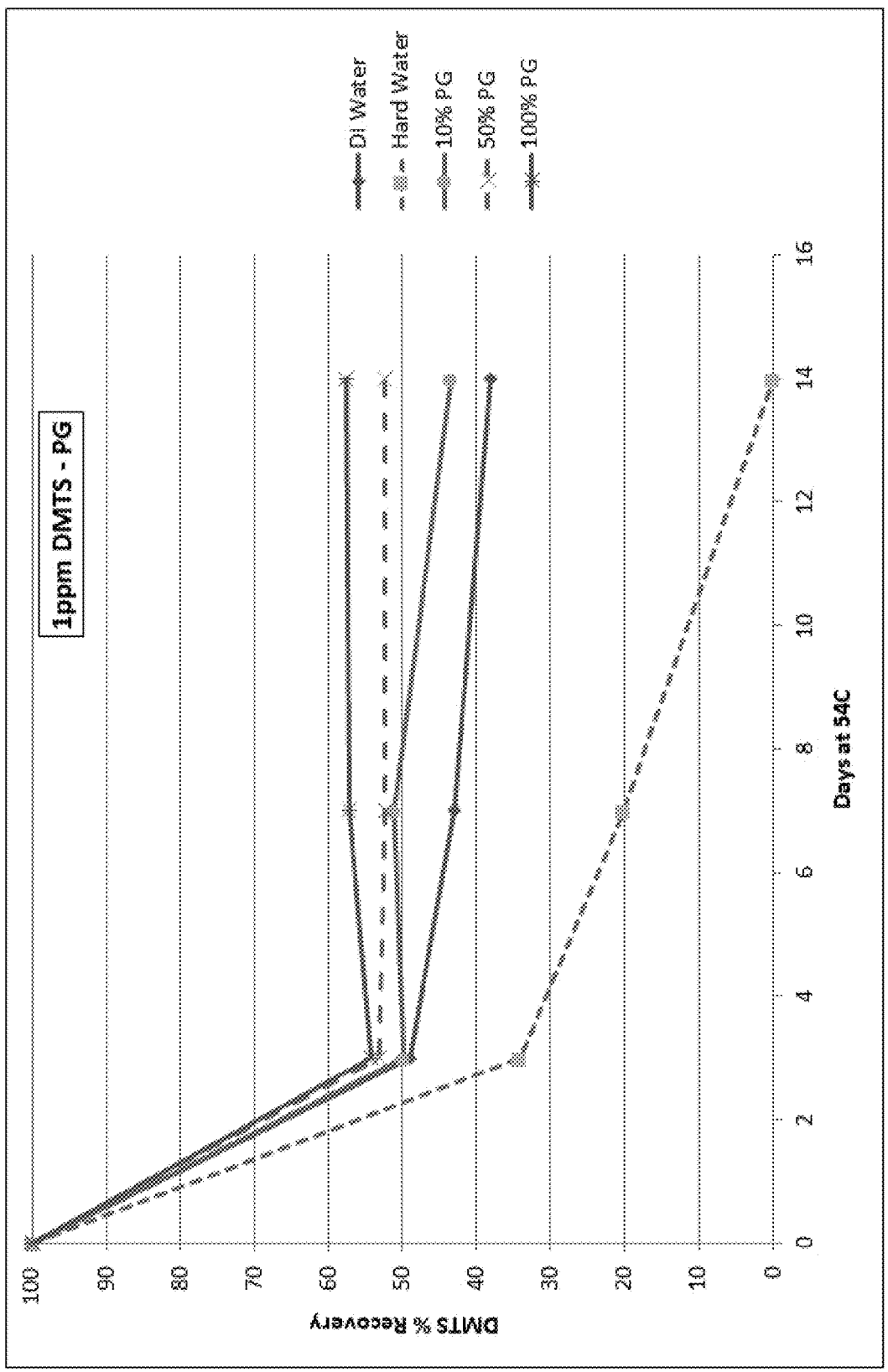
FIG. 12 is a line graph showing DMTS recovery over time comparing solvents having different concentrations of propylene glycol in water.

FIG. 12 shows similar results when the solutions include PG. Addition of PG to water improved DMTS stability, but even at 100% PG, recovery was less than 60%.

Example 11

In this example, various concentrations of DMTS in water, ethanol (EtOH), and propylene glycol (PG), with and without MDEA, were prepared and tested for degradation. The pH was adjusted to 2, 7, or 12+/−0.5 with sodium hydroxide or hydrochloric acid. The DMTS concentration was measured by gas chromatograph on Day 0 and Day 14 and the percent degradation calculated from those values. The formulas were capped and stored at 54° C. for two weeks. The results are shown below in Table 3.

TABLE 3

DMTS Degradation Over 14 Days at 54° C.

| Formula | DMTS Conc. | Diluent | MDEA Present | pH | % Degradation |
|---|---|---|---|---|---|
| 1 | 50 ppm | Water | 0 ppm | 7 | 13 |
| 2 | 50 ppm | 5% PG | 0 ppm | 7 | 16 |
| 3 | 50 ppm | 50% PG | 0 ppm | 7 | 4 |
| 4 | 50 ppm | 95% PG | 0 ppm | 7 | 1 |
| 5 | 50 ppm | Water | 0 ppm | 12 | 53 |
| 6 | 50 ppm | Water | 200 ppm | 2 | 20 |
| 7 | 50 ppm | Water | 200 ppm | 12 | 100 |
| 8 | 50 ppm | 50% PG | 200 ppm | 7 | 90 |
| 9 | 50 ppm | 95% PG | 200 ppm | 7 | 1 |
| 10 | 50 ppm | 50% PG | 200 ppm | 2 | 67 |
| 11 | 50 ppm | 95% PG | 200 ppm | 2 | 4 |
| 12 | 50 ppm | 50% PG | 200 ppm | 12 | 100 |
| 13 | 50 ppm | 95% PG | 200 ppm | 12 | 100 |
| 14 | 2800 ppm | 100% PG | 0 ppm | 7 | 6 |
| 15 | 2800 ppm | 100% PG | 11000 ppm | 7 | 31 |
| 16 | 300 ppm | 100% EtOH | 0 ppm | 7 | 3 |
| 17 | 300 ppm | 100% PG | 0 ppm | 7 | 8 |
| 18 | 250 ppm | 100% PG | 0 ppm | 7 | 1 |
| 19 | 8 ppm | Water | 0 ppm | 7 | 26 |
| 20 | 8 ppm | Water | 32 ppm | 7 | 97 |
| 21 | 8 ppm | Water | 0 ppm | 7 | 38 |
| 22 | 8 ppm | 1% PG | 0 ppm | 7 | 23 |
| 23 | 8 ppm | 10% PG | 0 ppm | 7 | 20 |
| 24 | 32 ppm | 10% PG | 0 ppm | 7 | 15 |
| 25 | 32 ppm | Water | 0 ppm | 7 | 27 |
| 26 | 32 ppm | Water | 0 ppm | 7 | 26 |
| 27 | 32 ppm | 5% EtOH | 0 ppm | 7 | 24 |
| 28 | 32 ppm | 50% EtOH | 0 ppm | 7 | 6 |
| 29 | 32 ppm | Water | 128 ppm | 7 | 98 |
| 30 | 10 ppm | Water | 40 ppm | 7 | 97 |
| 31 | 3 ppm | Water | 12 ppm | 7 | 100 |
| 32 | 3 ppm | Water | 0 ppm | 7 | 4 |

Table 3 shows that when water is selected as the diluent and MDEA is not present, 40% or more of DMTS remains after the two weeks of testing at 54° C. when the pH is neutral (pH=7; see formulas 1, 19, 21, and 32). When MDEA is added to the water and DMTS at neutral pH, the almost all of it is degraded after two weeks at 54° C. (e.g., formula 20) but when the pH is lowered to 2, only 20% of the DMTS is degraded after two weeks of storage at 54° C. This shows that water can be a suitable carrier for DMTS at neutral and acidic pH values and DMTS+MDEA at acidic pH values and that such formulas do not show a significant amount of DMTS degradation after two weeks at 54° C. and that the formulas are stable as a one-part composition.

Table 3 also shows that at a neutral pH (pH=7), a 50/50 mixture of water and propylene glycol can further reduce the amount of DMTS that is degraded. Compare formulas 1 and 3. The amount of DMTS that is degraded is reduced even more when the dilute is 95% propylene glycol. (See formula 4.) When MDEA is added to DMTS, a 50/50 mixture of propylene glycol and water is not sufficient to prevent the DMTS from degrading at a neutral pH. See formula 8 showing 90% of the DMTS is degraded after two weeks at 54° C. But, increasing the propylene glycol concentration to 95% at a neutral pH (formula 9), reducing the pH from 7 to 2 (formula 10), or both (formula 12) decreases the amount of DMTS that is degraded.

Table 3 also shows that ethanol is also a good diluent for maintaining the DMTS concentration. A 50/50 combination of ethanol and water resulted in only 6% degradation in DMTS after two weeks at 54° C. at a neutral pH (formula 28 versus formulas 25-27). Increasing the ethanol concentration to 100% of the diluent reduced that degradation to only 3% at a neutral pH, even when the concentration of DMTS was increased from 32 ppm to 300 ppm (formula 16).

While certain embodiments have been described, other embodiments may exist. While the specification includes a detailed description, the scope of the present disclosure is indicated by the following claims. The specific features and acts described above are disclosed as illustrative aspects and embodiments. Various other aspects, embodiments, modifications, and equivalents thereof which, after reading the description herein, may suggest themselves to one of ordinary skill in the art without departing from the spirit of the present disclosure or the scope of the claimed subject matter.

The invention claimed is:

1. A single-phase composition comprising:
10 ppm to 2800 ppm dimethyl trisulfide (DMTS);
120 ppm to 120,000 ppm amine selected from the group consisting of trimethylamine, isopropylamine, trimethanolamine, monoethanolamine, diethanolamine, triethanolamine, methyl diethanolamine, bicine, histamine and mixtures thereof;
at least 80 wt. % polar organic solvent; and
a pH of 1 to 7;
wherein the composition is free of water or contains no more than 10 wt. % water and the DMTS does not degrade more than 40% within one year of storage, and the composition is phase-stable in containers.

2. The single-phase composition of claim 1, wherein the composition comprises 30 ppm to 1000 ppm DMTS.

3. The single-phase composition of claim 1, wherein the DMTS does not degrade more than 30% over a period of one year of storage.

4. The single-phase composition of claim 1, wherein the composition comprises at least 90 wt. % polar organic solvent.

5. The single-phase composition of claim 1, wherein the composition comprises less than 1 wt. % water.

6. The single-phase composition of claim 1, wherein the composition comprises from 120 ppm to 1,200 ppm amine.

* * * * *